United States Patent [19]

Djorup

[11] Patent Number: 4,793,182
[45] Date of Patent: Dec. 27, 1988

[54] CONSTANT TEMPERATURE HYGROMETER

[76] Inventor: Robert S. Djorup, 20 Lovewell Rd., Wellesley, Mass. 02181

[21] Appl. No.: 57,034

[22] Filed: Jun. 2, 1987

[51] Int. Cl.[4] .............................. G01W 1/00
[52] U.S. Cl. ...................... 73/336.5; 73/29
[58] Field of Search ................. 73/336.5, 29

[56] References Cited

U.S. PATENT DOCUMENTS

| | | | |
|---|---|---|---|
| 1,855,774 | 4/1932 | Schneider . | |
| 2,237,006 | 4/1941 | Koller | 201/63 |
| 3,075,385 | 1/1963 | Stover | 73/335 |
| 3,164,004 | 1/1965 | King | 73/23 |
| 3,253,219 | 5/1966 | Littler | 324/71 |
| 3,350,941 | 11/1967 | Misevich et al. | 73/336.5 |
| 3,523,244 | 8/1970 | Goodman et al. | 324/61 |
| 3,582,728 | 6/1971 | Thoma | 317/246 |
| 3,802,268 | 4/1974 | Thoma | 73/336.5 |
| 4,143,177 | 3/1979 | Kovac et al. | 427/79 |
| 4,164,868 | 8/1979 | Suntola | 73/336.5 |
| 4,501,147 | 2/1985 | Niwa | 73/336.5 |
| 4,562,725 | 1/1986 | Oka et al. | 73/29 |
| 4,662,220 | 5/1987 | Laue | 73/336.5 |

OTHER PUBLICATIONS

Wexler, A., "Electric Hygrometers", United States Department of Commerce, National Bureau of Standards Circular 586, Sep. 3, 1957.
King, W., Jr., "Using Quartz Crystals as Sorption Detectors... part 1", Research/Development, Apr., 1969, pp. 28-33.
Perry, A. E., "Constant Temperature Hot-Wire Anemometers for the Measurement of Velocity Fluctuations", Hot-Wire Anemometry, 1982, pp. 59-64.
Asch, G., Les Capteurs en Instrumentation Industrielle, Chapter 17, pp. 705-732, published by Dunod (Bordas) Paris, 1983, ISBN 2-04-015635-6.
Krigman, A., "Moisture and Humidity 1985: An Emphasis on Sensor Development", INTECH, Mar. 1985, pg. 9.

*Primary Examiner*—Stewart J. Levy
*Assistant Examiner*—Joseph W. Roskos

[57] ABSTRACT

A constant temperature hygrometer comprising a piezoelectric substrate supporting a temperature coefficient resistor on one face and a conducting electrode on the opposite face, one or both conductor faces partially or completely covered by a hygroscopic layer of aluminum oxide anodized from aluminum metal deposited on one or both conductor faces, operated by a feedback controlled constant temperature bridge circuit, excited and read out by radio frequency oscillator circuitry; together with alternate forms of hygrometer transducer structures and water vapor sorptive materials.

20 Claims, 3 Drawing Sheets

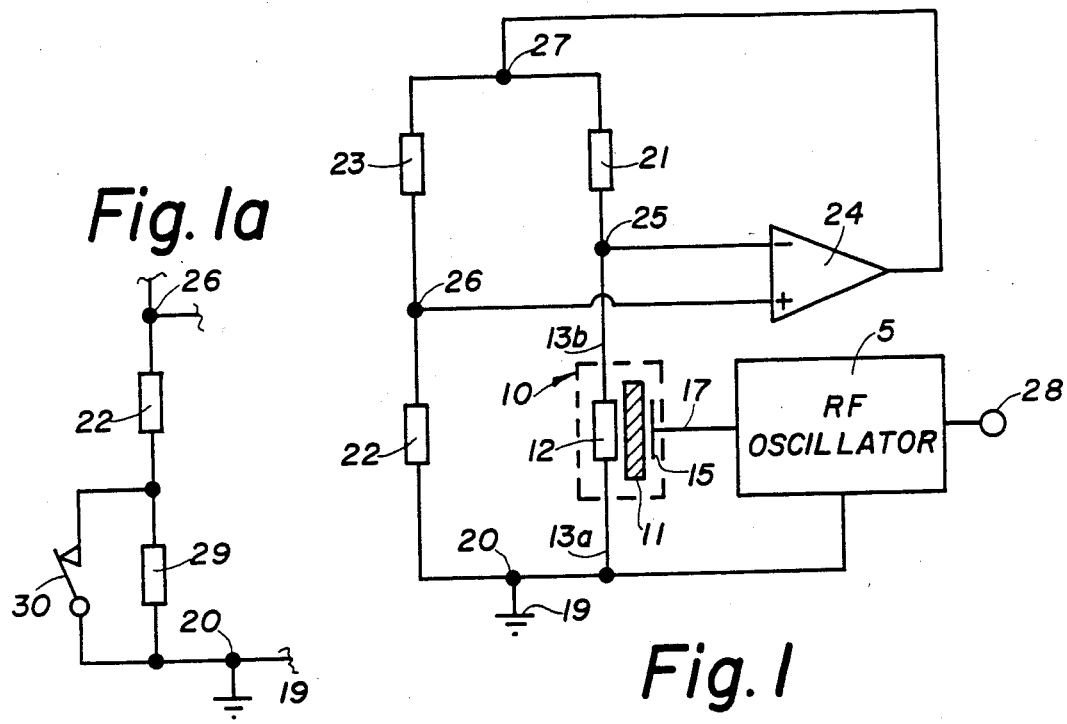
Fig. 1a
Fig. 1
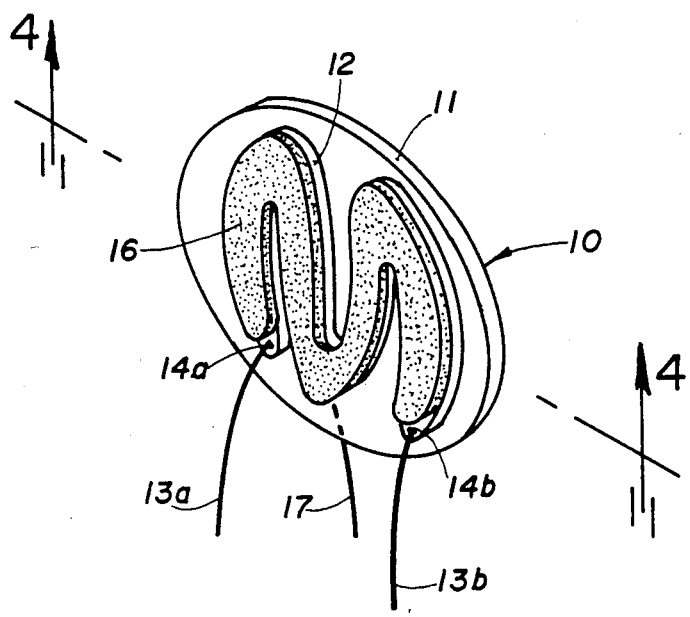
Fig. 2
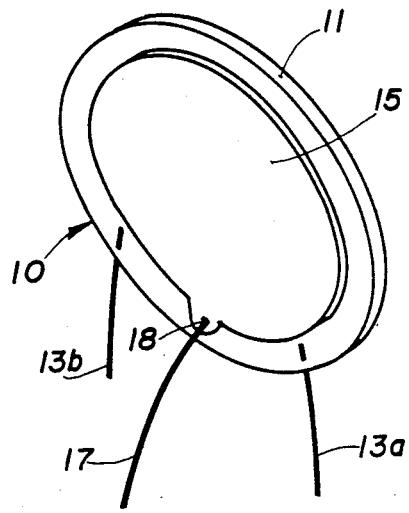
Fig. 3
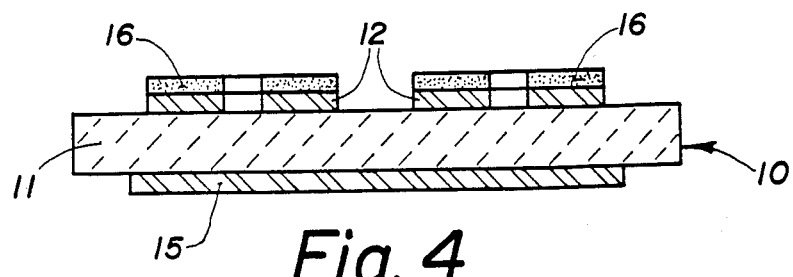
Fig. 4

CONSTANT TEMPERATURE HYGROMETER

BACKGROUND OF THE INVENTION

This invention relates generally to improved hygrometer apparatus for measuring atmospheric water vapor content The invention is particularly concerned with hygrometer transducer constant temperature operating apparatus and sorption hygrometer transducer apparatus that have sensitive and stable performance, and which may be fabricated simply and economically. The invention also includes constant temperature operation of refractory substrate-supported capacitance, resistance, and surface acoustic wave humidity transducers and substrate-supported transducers generally.

The art of electric hygrometry is a mature and well-developed art. Hygroscopic materials have been used as sorption detectors on crystal microbalances, as dielectrics in capacitors, and as coatings over electrodes which together operate as variable resistances. Among the more sensitive hygrometers are piezoelectri quartz crystal sorption hygrometers which work through the adsorption of water vapor onto a hygroscopic coating on an oscillating quartz crystal. The resulting increase in weight changes the frequency of oscillation by an amount proportional to the weight gain and the instrument functions as a very sensitive microbalance. Several examples of a microbalance mechanism used as a coated piezoelectric analyzer are given by U.S. Pat. No. 3,164,004 in which we are taught about various materials which may be used as sensitive coatings and we are also taught details of the microbalance technique. In 1969 William H. King, Jr. extensively described "Using Quartz Crystals as Sorption Detectors" on pages 28–34 and 28–33 of the April and May issues, respectively, of the journal "Research/Development". Microbalance technique is further taught by U.S. Pat. No. 3,253,219 which describes corrosion rate measurements using the crystal microbalance technique. Later, U.S. Pat. No. 4,562,725 teaches us about a family of moisture sensitive film coatings which may be used on microbalance crystals as well as on resistance transducers.

The use of metal oxides in moisture sensing, and aluminum oxide in particular, is taught by U.S. Pat. No. 2,237,006 which describes a capacitance type moisture sensor using aluminum oxide as a hygroscopic layer between capacitor plates. U.S. Pat. No. 3,075,385 further develops the approach using aluminum oxide as a dielectric in a capacitance hygrometer for radiosondes. U.S. Pat. Nos. 3,523,244 and 4,143,177 also describe capacitance hygrometers which use aluminum oxide as a moisture sensitive element between capacitor plates and the latter patent also teaches us the use of aluminum oxide and silicon dioxide as moisture responsive elements in semiconductor device constructions. In addition, we are taught about the use of separate heater resistors and temperature sensing resistors or semiconductors that are used in conjunction with the described oxide dielectric capacitance hygrometers.

Polymer films are widely used as moisture sensitive elements and U.S. Pat. No. 4,164,868 teaches us about the use of hygroscopic polymer films as dielectrics in capacitive humidity transducers. U.S. patents that describe and define other hygroscopic films in capacitance humidity transducers are U.S. Pat. Nos. 3,350,941; 3,582,728 and 3,802,268.

Prior art hygrometer sensors are generally operated at ambient temperature and can easily become loaded with moisture which limits their response Aluminum oxide humidity sensors often demonstrate poor calibration stability owing to ambient temperature operation. The reaction of aluminum oxide with water, as in the aluminum oxide-hydroxide reaction rate, manifests itself as calibration instability, often confused with hysteresis. Many of these same deficiencies are exhibited by capacitive hygrometer transducers which use hygroscopic film materials as a dielectric. In particular, if such transducers become wet or saturated, an extremely long time must pass until they dry off and again become responsive to atmospheric moisture change. The performance of certain capacitance hygrometer sensors is partially constrained or reduced by the presence of a necessary metal electrode on both faces of the hygroscopic layer.

SUMMARY OF THE INVENTION

The present invention overcomes many of the problems encountered by prior art hygrometer sensors and provides a significant improvement in hygrometer transducer performance and speed of response by employing controlled constant temperature operation of the active transducer element. In doing so, it is as if the entire surrounding environment around the transducer were at the controlled temperature. The hygrometer transducer is desorbed or dried off periodically or on demand. An improved constant temperature microbalance sorption hygrometer transducer as well as application of the improvement to other substrate-supported hygrometer transducers of the capacitance, resistance and surface acoustic wave type is disclosed.

The constant temperature hygrometer according to the instant invention includes an insulating substrate which supports a positive temperature coefficient resistive conductor, such as platinum metal, a sorptive coating over the conductor, a feedback controlled electrical circuit to operate the resistive conductor at constant temperature (constant resistance) and an electrical circuit, as required, to sense or read out the amount of sorbed water vapor. In a preferred embodiment the active sorptive coating is aluminum oxide which is anodized from aluminum metal deposited upon the platinum resistor. In this preferred embodiment the insulating substrate is a piezoelectric crystal, such as quartz, which also supports a second rf electrode. When the crystal electrode pair, the rf electrode and the resistive conductor, are connected into an rf oscillator circuit for crystal excitation, the combination of crystal supported transducer and the rf oscillator circuit together function as a sensitive crystal microbalance. With the resistive conductor connected into a feedback controlled Wheatstone bridge, used to control operation of the resistive conductor at a preset constant temperature above the surrounding ambient temperature, the combination becomes a constant temperature microbalance sorption hygrometer.

Embodiments are disclosed wherein the sorptive coating is applied to both electrodes and also over the entire transducer apparatus. An embodiment is disclosed where a second rf electrode is interdigitated with the resistive conductor in order to facilitate isolation of the constant temperature control and the rf oscillator circuit from each other. Further embodiments disclose alternative sorptive coatings as well as hygroscopic coatings. In yet further embodiments the use of constant temperature operation together with application of a temperature coefficient resistive conductor to substrate-supported capacitance, resistance, and surface acoustic wave humidity transducers is disclosed. Disclosure of the application of constant temperature operation of transducers, generally, is made wherein a temperature coefficient resistance is constructed within the transducer structure. The instant invention overcomes many of the problems associated with prior art hygrometer sensors respecting moisture loading and instability since the present invention operates the hygrometer sensors under optimum constant temperature conditions and also desorbs the hygrometer sensors on command. Maximum advantage may be taken of the sensitivity of microporous metal oxides by applying them to the disclosed transducer structure without a need to partially cover them with a metal electrode.

BRIEF DESCRIPTION OF THE DRAWING

FIG. 1 is a simplified electrical schematic of a preferred embodiment of constant temperature feedback control for a humidity sensing transducer made in accordance with the principles of the present invention;

FIG. 1a depicts a portion of the FIG. 1 schematic where structure for selecting alternate constant operating temperature of the humidity sensing transducer is shown;

FIG. 2 is a perspective view of a preferred embodiment of a humidity sensing transducer made in accordance with the principles of the present invention;

FIG. 3 is a perspective view of the reverse side of the humidity sensing transducer illustrated by FIG. 2;

FIG. 4 is an elevational section view of the humidity sensing transducer of FIGS. 2 and 3;

DESCRIPTION OF THE PREFERRED EMBODIMENT

Figure 5:
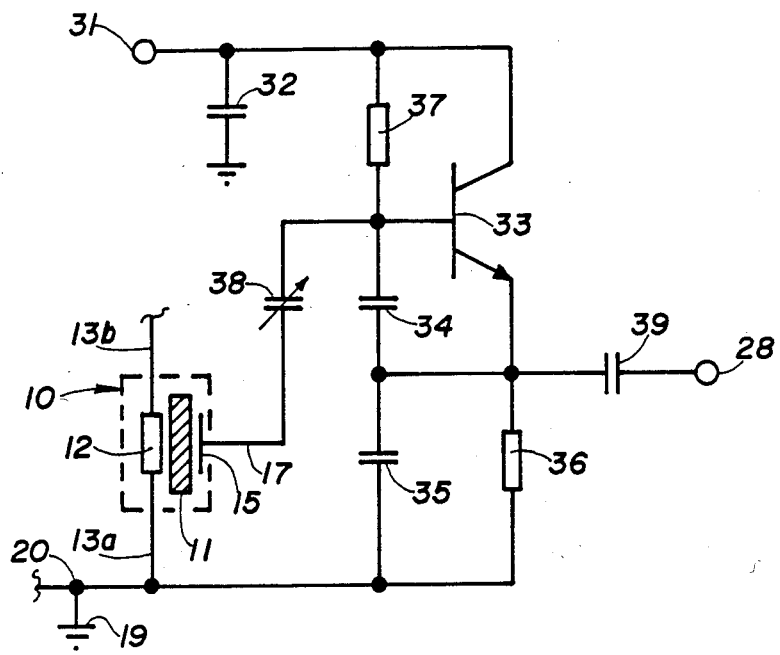
FIG. 5 is a simplified electrical schematic of a crystal oscillator circuit used to excite a piezoelectric crystal used as part of a three-terminal humidity sensing transducer made in accordance with the principles of the present invention.

An important feature of the invention is that a humidity sensing transducer element is operated at an automatically controlled constant temperature whereby uniform sensitivity to water vapor is repeatably established and the sensing element itself is easily cleared of moisture upon command without compromising speed of response. A preferred embodiment of the invention is shown in FIG. 1 wherein a constant temperature microbalance sorption hygrometer is described. A microbalance mechanism 10 uses a piezoelectric substrate 11 that has a conductor coating 12 and 15 on its two faces. Conductor coating 12 is in the form of a resistance conductor pattern which has two terminals 13a and 13b for electrical connections. The deposited conductor coating 12 is a high temperature coefficient of resistance metal such as platinum so that the same resistor 12 can be used as a heater element and simultaneously detect its own self-resistance when operated in a feedback controlled Wheatstone bridge 12, 21, 22, 23 electrical circuit with a differential amplifier 24 used to close the feedback control loop and provide bridge excitation. The resistance conductor pattern 12 is coated with a thin layer of aluminum metal that is anodized to convert the aluminum metal layer to a thin microporous aluminum oxide coating 16 (FIG. 2) capable of adsorption of water vapor molecules. Generally, solid surfaces and metal oxides tend to adsorb gases to lower their surface energy. It is the aluminum oxide coating 16 that is responsive to changes in ambient humidity or atmospheric water vapor content. Aluminum oxide sorption hygrometers are notable for their intrinsic fast response owing to thinness of the aluminum oxide coating coupled with high adsorption efficiency. Some $7.7 \times 10^{10}$ pores per square centimeter with a diameter of 100 to 300 Angstroms are obtained with an effective adsorption surface area of up to 0.2 square meters per square centimeter of aluminum oxide coating 16. Humidity measurement is effected by literally weighing the amount of water vapor that is sorbed into the aluminum oxide layer 16 on conductor 12. As sorbed moisture increases, the crystal 11 surface becomes mass-loaded and its frequency of radio frequency (rf) oscillation is decreased thereby providing a measure of humidity at an oscillator 5 output 28. Aluminum oxide sorption hygrometers respond to the vapor pressure of water over a very wide range of vapor pressures. As a rule, the amount of sorption is proportional to the water vapor partial pressure and inversely proportional to the absolute temperature. The strong affinity of water for aluminum oxide makes these devices highly selective towards water. They do not respond to most other common gases nor to numerous organic gases and liquids. A thick aluminum oxide layer, upwards of 1 $\mu$m, shows predominantly relative humidity characteristics while with a thin aluminum oxide layer below 0.3 $\mu$m an absolute humidity characteristic predominates.

Platinum is the preferred material for conductor coating 12 because of its stability, electrical characteristics, and resistance to oxide formation. Nickel may also be used for conductor coating 12 although maximum processing temperatures are substantially lower than those for platinum in order to avoid the nickel Curie point of 358° C. above which nickel is subject to oxidation. Since the useful oxide layer is the aluminum oxide layer 16, stray oxidation of other metals used in transducer construction can degrade hygrometer performance. Processing methods for both platinum and nickel differ and may become a factor in transducer material selection and manufacture. When nickel is to be used as resistive conductor 12, vacuum deposition of nickel and either electrochemical or vacuum deposition of the aluminum metal layer 16 can avoid high processing temperatures.

Conductor coating 15 (FIG. 3), on the opposite face of crystal substrate 11, may also be made of platinum and it is used as a capacitor plate or rf electrode of crystal oscillator transducer element 00. Radio frequency electrode 15 is connected to the oscillator circuit 5 by a lead wire connection 17. Crystal substrate 11 is the capacitor dielectric. When sorbed water vapor is detected at constant temperature in the local environment of the crystal's heated surface, and above the dew point temperature, repeatable and unambiguous operating conditions obtain so that a useful humidity measurement can be made using a single crystal oscillator. Frequency drift of the temperature controlled crystal oscillator becomes negligibly small when compared to the oscillator frequency excursions brought about by the oxide layer water vapor sorption From time to time, or when the transducer is accidentally soaked with water, the active aluminum oxide layer 16 may be desorbed or dried off by elevating the resistance conductor pattern 12 temperature above that of the boiling point of water. Rapid response of the hygrometer is enhanced by the constant elevated operating temperature of the adsorptive layer 16 above the expected maximum dew point temperature so that it never becomes saturated with water vapor. A primary function of resistive conductor coating 12 is to heat the aluminum oxide layer 16 which is in extremely close contact and a secondary function of conductor 12 heating is to maintain the crystal oscillator substrate 11 at the same constant temperature or within a narrow temperature range. The other side of the crystal 11, supporting electrode 15, will be at a slightly lower temperature owing to thermal lagging of the heat flow from conductor coating 12 through crystal dielectric 11 and also due to local convection cooling losses. The resulting humidity sensing transducer element is a three-terminal electrical device consisting of an oxide coated resistor and a capacitor with a piezoelettric dielectric, both circuit elements sharing one electrical terminal and a common substrate. The transducer element functions as a constant temperature microbalance sorption hygrometer when the resistance element is included as one arm of a feedback controlled Wheatstone bridge with driver amplifier and the capacitor element is excited by radio frequency oscillator circuit means, thereby providing means for signal readout representing humidity measurement as indicated by a frequency excursion.

Although the preferred embodiment describes an aluminum oxide layer coating the resistance heater electrode, it should be understood that hygrometer transducer sensitivity can be increased by applying the sorptive coating on both faces of the crystal substrate, covering both the areas of resistive conductor 22 and rf electrode 15. In the limit, the crystal substrate 11 with conductors 12 and 15 can be completely coated with aluminum metal which is then anodized to form aluminum oxide over the entire transducer 10 although this requires that extreme care must be taken to convert the entire aluminum coat to its oxide form. Where the transducer element 10 is intended for high temperature applications, it is preferable to deposit the aluminum coating only on the platinum conductor coating areas 12 and 15 since it is necessary to completely oxidize every bit of the aluminum metal layer to aluminum oxide in order to assure temperature stability.

Referring again to FIG. 1, resistive conductor 12 with series power resistor 21 form the high current or driven arms of a four arm Wheatstone bridge that is completed by resistors 22 and 23 which form the reference arms of the bridge. Since resistive conductor 12 is a platinum resistor that has a high positive temperature coefficient of resistance, any current flow will cause self heating together with an increase in resistance of conductor 12. Resistors 21, 22 and 23 all have a near-zero or low temperature coefficient of resistance, and self-heating owing to current flow causes negligible resistance change. When the resistance ratios of resistor 23 to 22 and 21 to 12 are the same, no error signal is developed between points 25 and 26 and no current will be fed to the top of the bridge at point 27 by differential amplifier 24 whose inputs are connected across the bridge at points 25 and 26. The bridge return 20 is connected to ground 19. A small offset voltage must be present at the output of amplifier 24 when the circuit is first turned on, and the resistive conductor 12 is at ambient temperature, so that a minute bridge current which flows as a result of the offset voltage is sufficient to develop a small error signal between the points 25 and 26, thus permitting the circuit to turn itself on to an operating condition. The resistance value of resistor 22 is selected to establish bridge balance at the desired elevated constant temperature operating point for resistive conductor 12 and the feedback loop operates to automatically adjust the current through the bridge until the resistance of resistive conductor 12 rises to attain that value of resistance which balances the bridge. The aforedescribed mode of operation has been described as a constant temperature (constant resistance) method of operation which is well known in the art of thermal anemometry.

A detailed discussion of the constant temperature anemometer circuit can be found on pages 59–64 of a book entitled "Hot-wire Anemometry" by A. E. Perry, published in 1982 by Oxford University Press, Oxford, England, listed as ISBN 0-19-856327-2, and also published in the United States by Oxford University Press, New York, N.Y.

In a typical bridge circuit the resistance of conductor 12 may, for example, be 5 ohms at a room temperature of 18° C. The power resistor 21 can be ohms and it has a low temperature coefficient of resistance, and adequate physical size, so that self heating does not cause appreciable change in its nominal resistance value with varying operating current levels since it must pass the full heating current for resistive conductor 12. With a nominal temperature coefficient of resistance of 3800 ppm/° C. resistive conductor 12 will be at a resistance value of about 5.608 ohms for a temperature of 50° C. If resistor 23 is 499 ohms the value of resistor 22 required to set the bridge in balance is 1399.2 ohms for a resistive conductor 12 self heating temperature of 50° C. The boiling point of water, 100° C., may be reached with a value of 1636.2 ohms for resistor 22.

FIG. 1a shows a portion of the Wheatstone bridge of FIG. 1 wherein a resistor 29 is placed in series with the resistor 22 in the same bridge arm together with a switch 30, connected across resistor 29, shown in a closed position short-circuiting resistor 29. When switch 30 is closed, the circuits of FIGS. 1 and 1a are electrically identical. If resistor 29 is 237 ohms, opening switch 30 will increase the total resistance of resistors 22 and 29 to 1636.2 ohms and cause the controlled temperature of resistive conductor 12 to rise to 100° C. A 355.5 ohm resistance value for resistor 29 will increase the controlled temperature to 125° C. for resistive conductor 12 which is high enough to effectively desorb the aluminum oxide layer 16, boiling off all sorbed water vapor. Normal sorption hygrometer operation of transducer 10 occurs again with closure of switch 30. Switch 30 may be a toggle switch, a remotely operable semiconductor switch, a digital switch or any equivalent locally or remotely operable switch Switching together with selected reference resistor provides a method for random non-periodic or programmed cyclic sorption/desorption operation of transducer 10. Although a series resistor connection has been shown for reference resistor selection, parallel resistor combinations as well as plurally selected combinations together with switch selection is equally effective.

FIG. 2 is a perspective view of a preferred embodiment of a humidity sensing transducer 10 constructed in accordance with the principles of the present invention. It is electrically described under FIG. 1. Transducer 10 is constructed upon substrate 11 which is a piezoelectric dielectric such as a quartz crystal intended for operation as an rf oscillator in the 1 to 20 MHz range. A typical crystal blank is about one centimeter in diameter and 0.016 centimeters thick and a prepared and coated crystal, when connected to an electrical oscillator circuit, oscillates at a natural resonant frequency of about 9 MHz. Generally, a standard 10 MHz fundamental-mode thickness-shear AT-cut quartz crystal blank is used since it has a broad temperature range where the frequency is almost constant and surface motion in a properly cut crystal is nil. Piezoelectric materials such as tourmaline, Rochelle salts, barium titanate, ammonium dihydrogen phosphate and others may also be used although quartz crystal blanks are the most widely available at modest cost. Quartz crystal blanks are obtainable from Bliley Electric Co., CTS Corp., Valpey-Fisher Corp., and many other sources.

Resistive conductor pattern 12 is applied in a serpentine or zig-zag pattern to increase its resistance and maintain uniform coverage and resistance distribution along the resistance path length. Alternatively, it may be applied over the entire face of substrate 11 and then cut away or trimmed to form a long and uniform electrical path length resistor. Cutting or shaping the resistor pattern may be accomplished by laser trimming techniques or by a gas propelled abrasive trimmer. Platinum metal is preferred material for resistive conductor 12 and may easily be applied by use of the "paint and fire" or "paint and bake" techniques. Platinum paste is literally printed onto the substrate 11 by using the methods employed by the thick film micro-circuit industry. An example of platinum paste, now called platinum ink by the trade, is Englehard Industries #6082 or #6926 which is used as if it was printer's ink. The resistor pattern can be applied by silk screen printing or by roll transfer, transferring the squeezed paste from a glass or polished metal plate to the crystal substrate by means of a soft rubber roller. Silk screen application is advantageous in that uniform films are easily applied and a defined resistor pattern is readily reproduced from unit to unit at low cost. After drying, the printed substrate 11 is fired in air at 800° to 850° C. by using an electric kiln or conveyor furnace. Reducing atmospheres are to be avoided.

After the platinum resistance conductor 12 is fired, and trimmed if needed, a layer of aluminum metal 16 is applied over resistive conductor 12 leaving areas 14a and 14b clear of aluminum metal so that lead wires 13a and 13b can later be attached. The aluminum layer can be applied by using aluminum ink, electrodeposition, or vacuum evaporation techniques. The use of aluminum ink is least costly and requires no exotic or complex fabrication equipment. Examples of aluminum inks are Engelhard Industries #A-3113 and #A-3484. Aluminum inks are also fired in air and at temperatures in the 550° to 675° C. range. Under certain conditions, firing temperatures to 900° C. may be needed to be employed for #A-3113 ink if molecular bonding to the substrate itself is intended. The lower temperatures may be used where the aluminum is placed directly over the platinum metal conductor which has a slightly matte surface finish after firing. The higher temperature is indicated if the entire face of the crystal is to be coated with aluminum metal.

After firing, the surface layer 16 of aluminum is oxidized to form a micro-porous aluminum oxide layer, also shown as 16 in FIG. 2 because of the complete material conversion which is to take place. Typically, the oxide may be formed by an anodizing process in which an alternating current is passed through a heated sulphuric acid solution containing suspended transducer 10 where electrical connection is made by clip to the area 14a or 14b of resistive conductor 12 which is uncoated by aluminum. The acid solution may include 20% to 70% sulphuric acid by volume and is externally heated, by suitable heating means, to a temperature of about 21° C. to 38° C. An alternating current of 54 to 270 amperes per square meter of anodizing surface passes through the solution while the transducer is suspended therein. The period of time ranges from 10 to 80 minutes depending on the percentage of acid in solution, solution temperature, current density, and the desired depth of the anodize. It has been reported in prior art patents and in instrumentation texts that satisfactory anodized coatings have been obtained by using a 50% sulphuric acid solution having a specific weight of 1.4 maintained at 90° F. (32.2° C.), with alternating current of 12 amperes per square foot (129 amperes per square meter) of anodizing surface during the anodizing for a period of 25 to 30 minutes.

After anodizing it may be necessary to stabilize the aluminum oxide ($Al_2O_3$) coating in order to avoid change in moisture adsorption qualities as a function of time and exposure. This can be accomplished by boiling the transducer 10 in distilled water for a period of 30 to 45 minutes after which the surface is scrubbed with a brush to remove the fairly loose layer of aluminum oxide powder which may have formed during boiling water aging. This leaves the hard stable form of hydrated aluminum oxide, the monohydrate or crystalline modification called boehmite ($\gamma$-$Al_2O_3 \cdot H_2O$).

When both sides of substrate 11 are appropriately coated, lead wires 13a and 13b are attached to clear platinum areas 14a and 14b by either use of spring-like clips, by microwelding, or by soft soldering to provide electrical connections to conductor 12. Lead wires 13a and 31b can be tinned copper, nickel, plated steel or other suitable material. If solder is used particular attention must be paid to the use of a platinum-compatible solder when conductor pattern 12 is made of platinum since the use of conventional tin-lead soft solder may cause eventual solder joint failure as a result of the formation of an unstable amalgam with the platinum metal.

A final aging step that is analogous to solution annealing may be applied to the completely fabricated hygrometer transducer 10 in order to drive off impurities or hygroscopic materials picked up during manufacture, to stabilize the aluminum oxide "grain" size and reduce the presence of fissures and cracks. This may be accomplished by baking the transducer assembly at a temperature from 200° C. to 350° C. for a period of time between 30 and 90 minutes.

FIG. 3 is a perspective view of the reverse side of humidity sensing transducer 10 illustrated by FIG. 2. A single rf electrode 55 is shown as a simple disc covering a majority of the face of crystal substrate 11 and it functions as one capacitor plate of the three-terminal hygrometer transducer 10. Electrode 15 may also be made of platinum metal which is applied in the same manner as that used to fabricate resistive conductor pattern 12. A single lead wire 17 is attached to area 18 in the same fashion as the leads 13a and 13b are attached to conductor 12. It is preferred, in order to avoid excessive mass loading of the surface of substrate crystal 11, to make all lead wire attachments, 14a, 14b and 18, at the outer edge or periphery of substrate 11 where oscillatory shear stresses are least pronounced.

FIG. 4 is an elevational section view of the humidity sensing transducer 10 structure illustrated in FIG. 2, taken along the line 4—4 thereof, and looking in the direction of the arrows. Piezoelectric crystal substrate 11 is shown supporting resistive conductor 12 and rf electrode 15 on opposite faces. The aluminum oxide coating 16 is shown covering resistive conductor 12. This sectional view makes it clear that resistive conductor 12 can also be used as a second capacitor plate of said three-terminal electrical device described under FIG. 1 as transducer 10.

FIG. 5 is a specific embodiment of an rf crystal oscillator circuit that may be used in accordance with the instant invention to excite a fundamental-mode piezoelectric crystal of a type herein described which is part of hygrometer transducer 10. A Colpitts oscillator circuit is illustrated although many other oscillator circuit means may be used, for example, the Pierce oscillator, the Hartley oscillator and its variants, the Schmitt trigger oscillator, the TTL oscillator, and many forms of other feedback oscillators whose design is well within the knowledge of those who are skilled in the art. The illustrated Colpitts oscillator is designed to operate with fundamental-mode crystals in the range of 1 MHz to 20 MHz. Typically, a collector supply voltage of +12 volts is applied to point 31 and radio frequency bypassed to ground by capacitor 32 which may be 0.01 microfarads. Transistor 33 is a type 2N2222, 2N4124 or similar general purpose silicon transistor. Feedback is controlled by capacitor voltage divider 34/35 with typical values of 82 picofarads and 0.001 microfarads, respectively. The rf voltage across 1,000 ohm emitter resistor 36 provides the basic feedback signal required to sustain circuit oscillation. Bia resistor 37 may be 220,000 ohms. Variable trimmer capacitor 38 may be up to 50 picofarads and is in series connection 17 with transducer 10 rf electrode 15. Transducer 10 second capacitor electrode; defined by connecting to the low potential side of resistive conductor 12, is connected to ground potential by lead wire 13a thus completing the oscillator circuit. Oscillator circuit rf signal output 28 is taken from the emitter of transistor 33 through a 0.001 microfarad coupling capacitor 39. Oscillator signal output frequency excursions for humidity variations from zero, or dry conditions, to saturation, range from $-10^2$ to $-10^4$ Hz for a typical humidity sensing transducer 10 constructed as herein described. A presence of 1 micron of water vapor at 50° C. can produce a signal shift of $-10$ to $-20$ Hz or better At lower operating temperatures sensitivity increases while transducer response time is lengthened. A typical 15 MHz crystal with 5 mm diameter electrodes has, for example, a predicted mass-loading sensitivity of about 2600 Hz per microgram. Similarly, a typical 10 MHz crystal with 7 mm diameter electrodes has a predicted mass-loading sensitivity of about 600 Hz per microgram. The detection limit has been estimated to be about $10^{-12}$ grams using the crystal microbalance weighing technique.

Figure 6:
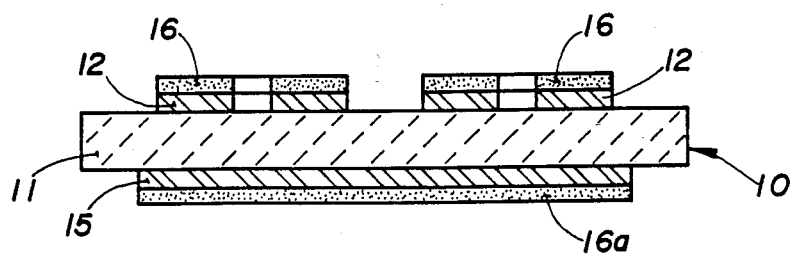
FIG. 6 illustrates a section view of a second embodiment of the humidity sensing transducer, similar to FIG. 4.

FIG. 6 illustrates a second embodiment of humidity sensing transducer 10, as an alternative to the section view of FIG. 4, wherein aluminum oxide sorptive coating 16 is shown on both faces of transducer 10, covering rf electrode 15 as well as resistive conductor 12. Coating both faces of the humidity sensing transducer 10 can effectively double the surface area of the water vapor sorptive coating of aluminum oxide 16 thereby resulting in a substantial increase in transducer sensitivity without excessively loading the piezoelectric crystal substrate 11.

Figure 7:
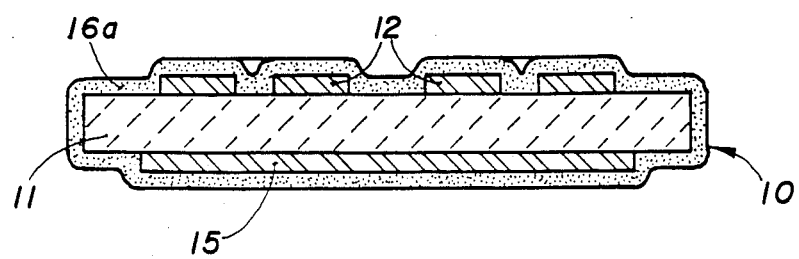
FIG. 7 is a cross-section view of a further embodiment of the humidity sensing transducer, similar to FIG. 4.

FIG. 7 illustrates a sectional view, as in FIG. 4, depicting a further embodiment of the humidity sensing transducer of FIG. 2, wherein the entire transducer 10 is covered with a sorptive coating 16a. Coating 16a may be aluminum oxide, a hygroscopic polymer or copolymer, deliquescent salts, or a similar moisture sensitive material. In general, aluminum oxide is a preferred effective long-lived sensitive coating but when lowest cost is a necessary factor the use of a dip-applied hygroscopic coating material becomes attractive. Many dipped coatings are problematic in use when the atmosphere becomes saturated or the coatings become wet, and they also often exhibit instability and hysteresis. Constant temperature hygrometer operation, as described by the instant invention, minimizes many of these shortcomings and, in certain applications, a cycle of desorption/sorption just prior to use can further enhance operation of the hygrometer, as in the case of expendable low-cost balloon-borne sondes. Typical hygroscopic polymers include hydroxyl ethyl cellulose, carboxyl methyl cellulose and cellulose esters. Examples of hygroscopic copolymers are vinylene carbonate and vinyl acetate among others. These materials may be solvent dissolved and they can be applied by simply dipping transducer 10 into the liquid material, then air dried or oven dried, followed by hydrolyzation of the coating by dipping the coated transducer 10 into an acid or alkaline bath for a period of time. The use of such materials and processing methods is taught by U.S. Pat. Nos. 3,350,941; 3,582,728 and 3,802,268, which describe the application of polymer and copolymer films to capacitance humidity transducers, and by U.S. Pat. No. 4,562,725 which describes moisture sensitive polymers and copolymers applied to piezoelectric moisture sensors.

Arnold Wexler's "Electric Hygrometers", published on Sept. 3, 1957, National Bureau of Standards Circular 586, U.S. Government Printing Office, Washington, D.C., further identifies useful sorptive coatings incuding metal oxide films, salt films and polymeric resins which may be applied to transducer 10 for use as the moisture sensitive coating 16a.

Figure 8:
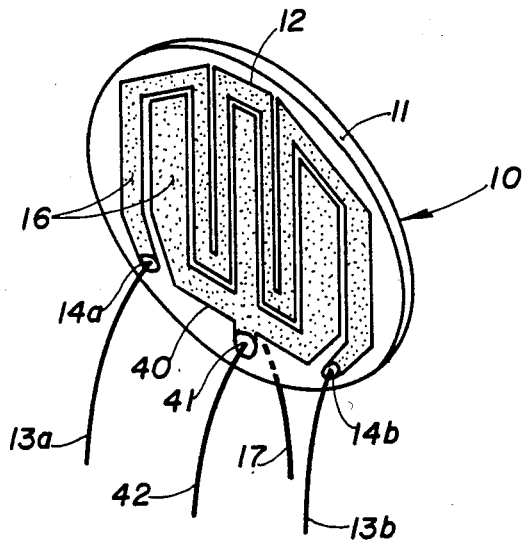
FIG. 8 is a perspective view of a further embodiment of the FIG. 2 humidity sensing transducer; and, FIG. 9 is a simplified electrical schematic of a specific embodiment of a crystal oscillator circuit used to excite a piezoelectric crystal used as a part of a four-terminal humidity sensing transducer depicted in FIG. 8.

FIG. 8 is a perspective view of a further embodiment of the humidity sensing transducer 10 of FIG. 2 depicting the addition of a second rf electrode 40, interlaced or interdigitated with resistive conductor pattern 12. Lead wire 42 is connected to rf electrode 40 at point 41. Provision of a second rf electrode 40 facilitates complete electrical isolation of the constant temperature control circuit of FIG. 1 from the rf oscillator circuit 5. Isolation of these circuits may be desired when the chosen oscillator circuit design requires that the rf electrodes 15 and 40 are operated away from electrical ground potential. In this embodiment, humidity sensing transducer 10 now becomes a four-terminal electrical device with two terminals connected to a capacitor element and two connected to a resistor element. Sorptive coating 16 is shown on both the resistive conductor pattern 12 and rf electrode 40. The reverse side of transducer 10 may be as described by FIG. 3.

Figure 9:
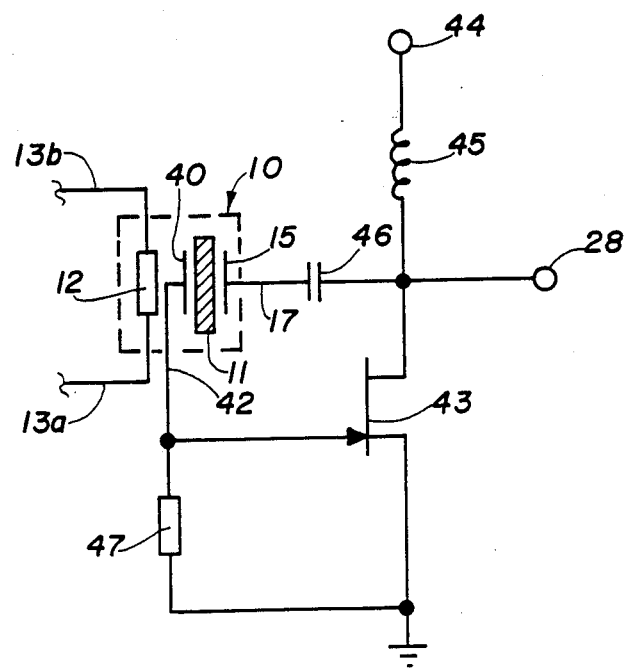

FIG. 9 is a schematic drawing of a JFET Pierce crystal oscillator circuit, among the least complex crystal oscillator circuits from the standpoint of design ease and least parts count. It is to be noted that rf electrodes 15 and 40 are both at an rf potential; therefore, transducer 10 capacitor section 15 and 40 should be separated from the transducer resistive conductor section 12, as shown in the four-terminal configuration for transducer 10 depicted by FIG. 8. The JFET crystal oscillator allows a wide frequency range of crystals to be used without circuit modification. Since the JFET gate does not load the crystal, good Q is maintained, thus insuring good frequency stability. Typically, junction field effect transistor 43 may be a general purpose type 2N5485 N-channel JFET suitable for rf amplifier use. A positive supply voltage in the 5 to 15 volt range at point 44 is connected through rf choke 45 to the drain of JFET 43 whose source is grounded. JFET 43 gate is connected to the junction of 10 megohm resistor 47 and transducer 10 electrode 40 lead wire connection 42. Transducer 10 rf electrode 15 is connected by lead wire 17 to 0.001 microfarad capacitor 46 which is also connected to JFET 43 providing an rf signal output at 28. Transducer 10 terminals 17 and 42 may be reversed without affecting performance. Transducer 10 terminals 13a and 13b, from resistive conductor pattern 12, are connected to the FIG. 1 constant temperature feedback control circuit hereabove described.

Yet a further embodiment of the invention is exemplified by the application of a non-zero temperature coefficient resistive conductor to other forms of substrate-supported hygrometer transducers and substrate-supported transducers generally, which are taught in the art, wherein said transducer is operated at a feedback controlled constant temperature as herein described. Said resistive conductor may be applied directly upon a substrate if said substrate is an electrically insulating material or, in the case of an electrically conducting substrate or non-insulator, said resistive conductor may be applied over a barrier insulating layer. Depending upon the transducer construction, an insulating layer or barrier layer may also be applied over the resistive conductor with the transducer structure next fabricated upon and over said layers. Typical insulating barrier materials are to be found among the dielectric glazes and protective coatings used by the semiconductor industry and thick film and thin film circuit industries. Examples of these are Engelhard Industries #A-3820, #A-3025, and #HD2008, among a wide variety of readily available materials. Silicon monoxide, silicon dioxide, and quartz also are a useful family of insulating materials which may be applied by vacuum deposition techniques. In the published art we are taught about different transducer types which may benefit by applications of the teachings of the instant invention. U.S. Pat. No. 4,143,177 exemplifies humidity sensors of the capacitance type employing a porous metallic oxide. Said sensors may be simplified, together with improved performance, by incorporation of controlled constant temperature resistive conductor means in place of separate resistance heater and resistance temperature detectors or semiconductor temperature sensors. Performance of the capacitance type aluminum oxide humidity sensor taught by U.S. Pat. No. 3,523,244 as well as the capacitive humidity transducers taught by U.S. Pat. No. 4,164,868 may both be enhanced and improved by application of the teachings of the instant invention respecting controlled temperature operation. A further example of a class of transducers which may benefit from the teachings and application of the instant invention are SAW (surface acoustic wave) devices which are used as substrates supporting gas detecting and chemical detecting films and coatings.

What is claimed is:

1. Hygrometer comprising:
   a piezoelectric substrate including a sorptive material affixed thereto;
   a heater adapted to maintain the substrate at a constant temperature;
   electrodes disposed on opposing sides of the substrate; and
   an oscillator circuit connected to the electrodes adapted to oscillate the substrate and to generate a signal proportional to oscillation frequency, the oscillation frequency being related to the amount of sorbed water.

2. The hygrometer of claim 1 wherein the heater comprises a temperature coefficient resistive conductor affixed to one surface of the substrate and a feedback controlled electrical circuit adapted to maintain the resistive conductor at a constant resistance.

3. The hygrometer of claim 2 wherein the sorptive material resides on the resistive conductor.

4. The hygrometer of claim 3 wherein the resistive conductor forms a serpentine pattern on the substrate.

5. The hygrometer of claims 2, 3 or 4 further including sorptive material on the second side of the substrate.

6. The apparatus of claim 1, 2, 3, or 4 wherein the sorptive material surrounds the substrate and electrodes.

7. The hygrometer of claim 2 wherein the resistive conductor is one of the electrodes on opposing sides of the conductor.

8. The hygrometer of claim 2 wherein the resistive conductor and electrodes are separate and are interdigitated on a surface of the substrate.

9. The hygrometer of claim 2 wherein the resistive conductor is one arm of a Wheatstone bridge and further including a differential amplifier to drive current through the resistive conductor to maintain its resistance and temperature constant.

10. The hygrometer of claim 9 wherein one arm of the Wheatstone bridge includes switching apparatus for varying the resistance of that arm to alter the constant resistance and temperature of the resistive conductor.

11. The hygrometer of claim 1 wherein the oscillator circuit is a Colpitts oscillator.

12. The hygrometer of claim 1 wherein the oscillator is a JFET Pierce crystal oscillator.

13. The hygrometer of claim 1 wherein the substrate is quartz.

14. The hygrometer of claim 1 wherein the substrate is a metal and includes a non-conductive barrier between the metal substrate and the electrodes.

15. The hygrometer of claim 1 wherein the sorptive material is aluminum oxide.

16. The hygrometer of claim 1 wherein the electrodes are platinum.

17. The hygrometer of claim 1 wherein the sorptive material is a hygroscopic polymer.

18. The hygrometer of claim 1 wherein the sorptive material is a hygroscopic copolymer.

19. The hygrometer of claim 1 wherein the sorptive material is a deliquescent salt.

20. Hygrometer comprising:
- a quartz substrate;
- a temperature coefficient resistive conductor disposed on a first surface of the quartz substrate;
- an aluminum oxide coating disposed on the resistive conductor;
- an electrode disposed on a second surface of the quartz substrate;
- a feedback controlled electrical circuit adapted to maintain the resistive conductor at a constant resistance; and
- an oscillator circuit connected to the electrode and to the resistive conductor adapted to oscillate the quartz substrate and to generate a signal proportional to oscillation frequency, the oscillation frequency being related to the amount of water sorbed by the aluminum oxide material.

* * * * *

UNITED STATES PATENT AND TRADEMARK OFFICE
CERTIFICATE OF CORRECTION

PATENT NO. : 4,793,182

DATED : December 27, 1988

INVENTOR(S) : Robert S. Djorup

It is certified that error appears in the above-identified patent and that said Letters Patent is hereby corrected as shown below:

Column 4, line 62, "00" should be --10--.
Column 5, line 6, "sorption" should be --sorption.--;
line 43, "22" should be --12--;
line 62, "self" should be --self- --.
Column 6, line 34, "self heating" should be --self-heating--;
line 43, "self heating" should be --self-heating--;
line 64, after "switch", insert --.--.
Column 7, line 41, "Englehard" should be --Engelhard--;
line 44, "squeezed" should be --squeegeed--.
Column 8, line 66, "55" should be --15--.
Column 9, line 6, "mass" should be --mass- --;
line 44, "Bia" should be --Bias--.

Signed and Sealed this

Ninth Day of May, 1989

Attest:

DONALD J. QUIGG

Attesting Officer

Commissioner of Patents and Trademarks